US012266427B2

(12) United States Patent
Kudo

(10) Patent No.: US 12,266,427 B2
(45) Date of Patent: Apr. 1, 2025

(54) SUBSTANCE GROUP ANALYSIS AND SUMMARIZATION METHOD, DEVICE, AND MEDIUM

(71) Applicant: SHIMADZU CORPORATION, Kyoto (JP)

(72) Inventor: Yukihiko Kudo, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 460 days.

(21) Appl. No.: 17/471,761

(22) Filed: Sep. 10, 2021

(65) Prior Publication Data

US 2022/0101956 A1 Mar. 31, 2022

(30) Foreign Application Priority Data

Sep. 29, 2020 (JP) ................. 2020-163940

(51) Int. Cl.
*G16C 20/80* (2019.01)
*G01N 30/62* (2006.01)
(Continued)

(52) U.S. Cl.
CPC ............. *G16C 20/80* (2019.02); *G01N 30/62* (2013.01); *G01N 30/8651* (2013.01);
(Continued)

(58) Field of Classification Search
CPC ........ G16C 20/80; G16C 20/20; G01N 30/62; G01N 30/8651; G01N 30/86; G01N 30/72;
(Continued)

(56) References Cited

U.S. PATENT DOCUMENTS

2006/0125826 A1* 6/2006 Lubkowitz ......... G01N 30/8675
345/440
2007/0181798 A1 8/2007 Lubkowitz et al.
(Continued)

FOREIGN PATENT DOCUMENTS

JP 2006-031084 A 2/2006
JP 2010-96642 A 4/2010
(Continued)

OTHER PUBLICATIONS

"Polybrominated diphenyl ethers", Wikipedia Foundation Inc., Jul. 28, 2020, 4pages.
(Continued)

*Primary Examiner* — Lisa M Caputo
*Assistant Examiner* — Cynthia L Davis
(74) *Attorney, Agent, or Firm* — Sughrue Mion, PLLC

(57) ABSTRACT

A processing apparatus for processing information relating an analysis, includes a display controller that causes a display device to display first information, which is information about each substance in regard to the analysis of a sample, and second information which is information about each substance group including a plurality of the different substances in regard to the analysis, wherein the display controller displays the first information and the second information to be switchable to each other or displays the first information such that a display and a non-display of the second information are switchable.

13 Claims, 9 Drawing Sheets

(51) Int. Cl.
  *G01N 30/86* (2006.01)
  *G06F 3/04842* (2022.01)
  *G06F 3/04845* (2022.01)
  *G16C 20/20* (2019.01)

(52) U.S. Cl.
  CPC ...... *G06F 3/04842* (2013.01); *G06F 3/04845* (2013.01); *G16C 20/20* (2019.02)

(58) Field of Classification Search
  CPC . G06F 3/04842; G06F 3/04845; G06F 3/0481
  See application file for complete search history.

(56) References Cited

U.S. PATENT DOCUMENTS

| | | | | |
|---|---|---|---|---|
| 2015/0160162 A1* | 6/2015 | Darland | ............ | H01J 49/0036 250/281 |
| 2018/0348180 A1* | 12/2018 | Kitano | ............... | G01N 30/8696 |
| 2020/0293558 A1 | 9/2020 | Hirao et al. | | |
| 2020/0309748 A1* | 10/2020 | Kudo | ................ | G01N 30/7206 |

FOREIGN PATENT DOCUMENTS

| | | | | |
|---|---|---|---|---|
| JP | 2019-032214 A | 2/2019 | | |
| JP | 2020-149600 A | 9/2020 | | |
| WO | WO-0013010 A2 * | 3/2000 | ......... | G01N 33/0075 |
| WO | 2018/008149 A1 | 1/2018 | | |

OTHER PUBLICATIONS

Japanese Office Action dated Aug. 29, 2023 in Japanese Application No. 2020-163940.
Japanese Office Action issued Jan. 30, 2024 in Application No. 2020-163940.
Multi-analyte Quantitation Software LabSolutions Insight (TM) manual, 2019, pp. 1-7 (16 pages total), https://www.an.shimadzu.co.jp/sites/an.shimadzu.co.jp/files/pim/pim_download_file/an_jp/brochures/2 0349/c191-0081.pdf.
Communication dated Aug. 27, 2024 issued by the Japanese Patent Office in application No. 2020-163940.

* cited by examiner

FIG. 2

CONTENTS IN SUBSTANCE DB (CHART A)

| SUBSTANCE GROUP | NAME OF SUBSTANCE | SET RETENTION TIME | TARGET IONS (m/z) | QUALIFIER IONS (m/z) | QUALIFIER ION RATIO |
|---|---|---|---|---|---|
| X | A | Ta | Qa | Ra | Rra |
| X | B | Tb | Qb | Rb | Rrb |
| X | C | Tc | Qc | Rc | Rrc |
| X | D | Td | Qd | Rd | Rrd |
| Y | E | Te | Qe | Re | Rre |
| Y | F | Tf | Qf | Rf | Rrf |
| Y | G | Tg | Qg | Rg | Rrg |
| Y | H | Th | Qh | Rh | Rrh |
| Z | I | Ti | Qi | Ri | Rri |
| Z | J | Tj | Qj | Rj | Rrj |
| Z | K | Tk | Qk | Rk | Rrk |

SCREEN SHOWING SUBSTANCE INFORMATION

SE1 (TS)

| SUBSTANCE GROUP | NAME OF SUBSTANCE | DETECTION | ACTUAL RETENTION TIME | CONCENTRATION | TARGET IONS (m/z) PEAK AREA VALUE | OF QUALIFIER IONS (m/z) PEAK AREA VALUE | ACTUAL QUALIFIER ION RATIO |
|---|---|---|---|---|---|---|---|
| X | A | ✓ | T'a | Ca | A(Q)a | A(R)a | Rr'a |
| X | B | ✓ | T'b | Cb | A(Q)b | A(R)b | Rr'b |
| X | C | ✓ | T'c | Cc | A(Q)c | A(R)c | Rr'c |
| X | D | ✓ | T'd | Cd | A(Q)d | A(R)d | Rr'd |
| Y | E | — | — | — | — | — | Rr'e |
| Y | F | ✓ | T'f | Cf | A(Q)f | A(R)f | Rr'f |
| Y | G | ✓ | T'g | Cg | A(Q)g | A(R)g | Rr'g |
| Y | H | — | — | — | — | — | Rr'h |
| Z | I | ✓ | T'i | Ci | A(Q)i | A(R)i | Rr'i |
| Z | J | ✓ | T'j | Cj | A(Q)j | A(R)j | Rr'j |
| Z | K | — | — | — | — | — | Rr'k |

SCREEN SHOWING SUBSTANCE GROUP INFORMATION

| SUBSTANCE GROUP | NUMBER OF SUBSTANCES | NUMBER OF DETECTED SUBSTANCES | SUMMED CONCENTRATION VALUE |
|---|---|---|---|
| X | 4 | 4 | Ca+Cb+Cc+Cd |
| Y | 4 | 2 | Cf+Cg |
| Z | 3 | 2 | Ci+Cj |

SE2 (TG)
C21　C22　C23　C24

FIG. 7
SCREEN SHOWING SUBSTANCE INFORMATION OR SUBSTANCE GROUP INFORMATION, IN REGARD TO EACH SUBSTANCE GROUP

SE4

| SUBSTANCE GROUP | NUMBER OF SUBSTANCES | NUMBER OF DETECTED SUBSTANCES | SUMMED CONCENTRATION VALUE |
|---|---|---|---|
| X | 4 | 4 | Ca+Cb+Cc+Cd |

TG1

| SUBSTANCE GROUP | SUBSTANCE NAME OF GROUP SUBSTANCE | DETECTION | ACTUAL RETENTION TIME | CONCENTRATION | TARGET IONS (m/z) PEAK AREA VALUE | QUALIFIER IONS (m/z) PEAK AREA VALUE | QULIFIER ION RATIO |
|---|---|---|---|---|---|---|---|
| Y | E | – | – | – | – | – | Rr'e |
| Y | F | ✓ | T'f | Cf | A(Q)f | A(R)f | Rr'f |
| Y | G | ✓ | T'g | Cg | A(Q)g | A(R)g | Rr'g |
| Y | H | – | – | – | – | – | Rr'h |
| Z | I | ✓ | T'i | Ci | A(Q)i | A(R)i | Rr'i |
| Z | J | ✓ | T'j | Cj | A(Q)j | A(R)j | Rr'j |
| Z | K | – | – | – | – | – | Rr'k |

SCREEN SHOWING SUBSTANCE INFORMATION AND SUBSTANCE GROUP INFORMATION, IN REGARD TO EACH SUBSTANCE GROUP  ─ SE5

| SUBSTANCE GROUP | SUBSTANCE NAME | DETECTION | ACTUAL RETENTION TIME | CONCENTRATION | TARGET IONS (m/z) PEAK AREA VALUE | QUALIFIER IONS (m/z) PEAK AREA VALUE | QUALIFIER ION RATIO |
|---|---|---|---|---|---|---|---|
| X | A | ✓ | T'a | Ca | A(Q)a | A(R)a | Rr'a |
| X | B | ✓ | T'b | Cb | A(Q)b | A(R)b | Rr'b |
| X | C | ✓ | T'c | Cc | A(Q)c | A(R)c | Rr'c |
| X | D | ✓ | T'd | Cd | A(Q)d | A(R)d | Rr'd |

─ TSX

| SUBSTANCE GROUP | NUMBER OF SUBSTANCES | NUMBER OF DETECTED SUBSTANCES | SUMMED CONCENTRATION VALUE |
|---|---|---|---|
| X | 4 | 4 | Ca+Cb+Cc+Cd |

─ TGX

| Y | E | — | — | — | — | — | Rr'e |
| Y | F | ✓ | T'f | Cf | A(Q)f | A(R)f | Rr'f |
| Y | G | ✓ | T'g | Cg | A(Q)g | A(R)g | Rr'g |
| Y | H | — | — | — | — | — | Rr'h |

─ TSY

| SUBSTANCE GROUP | NUMBER OF SUBSTANCES | NUMBER OF DETECTED SUBSTANCES | SUMMED CONCENTRATION VALUE |
|---|---|---|---|
| Y | 4 | 2 | Cf+Cg |

─ TGY

SUBSTANCE GROUP ANALYSIS AND SUMMARIZATION METHOD, DEVICE, AND MEDIUM

BACKGROUND

Technical Field

The present invention relates to a display method, an analysis method and a processing apparatus in regard to information relating to an analysis, and a non-transitory computer readable medium storing a program.

Description of Related Art

A sample is analyzed, and information about a substance group including a plurality of different substances is obtained. As shown in "Polybrominated diphenyl ethers," [online], Jul. 28, 2020, Wikipedia Foundation Inc, [searched on Aug. 25, 2020.], <URL: https://en.wikipedia.org/wiki/Polybronninated_diphenyl_ethers>, Polybrominated diphenyl ether (PBDE) represents a substance group including a plurality of substances having different positions or the different number of bromine atoms. According to the EU RoHS (Restriction of Hazardous Substances) directive, the upper limit for the content of PBDE in each component that constitutes an electrical/electronic product is 1 g/kg in regard to the summed value of a plurality of different substances included in this substance group. In an analysis of a sample in regard to a substance group, information about a substance group and each substance included in the substance group is displayed for examination of data, provision of notification of a result to an analyst, etc. At this time, the information to be displayed may be incomprehensible since a plurality of items in regard to a substance group and each substance are displayed. This problem is apparent in a case where a plurality of substance groups are examined, many substances are included in a substance group, etc.

SUMMARY

It is desirable to provide information about a substance group and substances included in the substance group in regard to an analysis of a sample in a comprehensible manner.

A display method of displaying information relating to an analysis according to one aspect of the present invention is a method of displaying information obtained from an analysis device for quantitatively analyzing a specific substance included in a sample that includes acquiring first information including a plurality of information pieces of a specific substance using the analysis device, classifying the first information into pre-registered substance groups such that each group includes a plurality of different substances, executing a statistical process of at least part of the first information in regard to each substance group and creating second information in regard to each substance group based on a result of the statistical process, and a screen display step of displaying at least one information out of the first information and the second information on a screen, wherein the screen display step includes receiving a display pattern selected by a user from among a pattern in which the first information and the second information are displayed at a same time on the screen, a pattern in which only the first information is displayed on the screen and a pattern in which only the second information is displayed on the screen, and changing a display pattern on the screen such that at least one information out of the first information and the second information is displayed in accordance with the received display pattern.

An analysis method according to another aspect of the present invention includes the above-mentioned display method of displaying information relating to an analysis.

A processing apparatus of processing information relating to an analysis according to yet another aspect of the present invention is a processing apparatus of displaying information obtained from an analysis device for quantitatively analyzing a specific substance included in a sample that includes a first information acquirer that acquires first information including a plurality of information pieces of a specific substance using the analysis device, a second information producer that classifies the first information into pre-registered substance groups such that each group includes a plurality of different substances, executes a statistical process of at least part of the first information in regard to each substance group and creates second information in regard to each substance group based on a result of the statistical process, and a display controller that displays at least one information out of the first information and the second information on a screen, wherein the display controller receives a display pattern selected by a user from among a pattern in which the first information and the second information are displayed at a same time on the screen, a pattern in which only the first information is displayed on the screen and a pattern in which only the second information is displayed on the screen, and changes a display pattern on the screen such that at least one information out of the first information and the second information is displayed in accordance with the received display pattern.

A non-transitory computer readable medium according to yet another aspect of the present invention stores a program for causing a computer to execute a display process of displaying information obtained from an analysis device for quantitatively analyzing a specific substance included in a sample on a screen, wherein the display process includes a process of acquiring first information including a plurality of information pieces of a specific substance using the analysis device, a process of classifying the first information into pre-registered substance groups such that each group includes a plurality of different substances, executing a statistical process of at least part of the first information in regard to each substance group and creating second information in regard to each substance group based on a result of the statistical process, and a screen display process of displaying at least one information out of the first information and the second information on a screen, and the screen display process includes a process of receiving a display pattern selected by a user from among a pattern in which the first information and the second information are displayed at a same time on the screen, a pattern in which only the first information is displayed on the screen and a pattern in which only the second information is displayed on the screen, and a process of changing a display pattern on the screen such that at least one information out of the first information and the second information is displayed in accordance with the received display pattern.

A processing apparatus according to yet another aspect of the present invention for processing information relating an analysis includes a display controller that causes a display device to display first information, which is information about each substance in regard to the analysis of a sample, and second information which is information about each substance group including a plurality of the different substances in regard to the analysis, wherein the display controller displays the first information and the second information to be switchable to each other or displays the first information such that a display and a non-display of the second information are switchable.

An analysis device according to yet another aspect of the present invention includes the processing apparatus for processing information relating to an analysis.

A display method according to yet another aspect of the present invention of displaying information obtained by an analysis, includes causing a display device to display first information, which is information about each substance in regard to an analysis of a sample, and second information, which is information about each substance group including a plurality of the different substances in regard to the analysis, wherein in a display, the first information and the second information are displayed to be switchable to each other, or the first information is displayed such that a display and a non-display of the second information is switchable.

A non-transitory computer readable medium according to yet another aspect of the present invention stores a program for causing a computer to execute a display process of causing a display device to display first information, which is information about each substance in regard to an analysis of a sample, and second information, which is information about each substance group including a plurality of the different substances in regard to the analysis, wherein the display process includes a process of causing the display device to display at least one of the first information and the second information such that the first information and the second information are displayed to be switchable to each other or the first information is displayed with the second information being switchable to be displayed or not to be displayed.

With the present invention, information about a substance group and substances included in the substance group in regard to an analysis of a sample can be provided in a comprehensible manner.

Other features, elements, characteristics, and advantages of the present disclosure will become more apparent from the following description of preferred embodiments of the present disclosure with reference to the attached drawings.

BRIEF DESCRIPTION OF THE DRAWING

FIG. 2 is a chart showing the contents of substance database according to the one embodiment;

FIG. 3 is a diagram showing one example of a screen showing substance information according to the one embodiment;

FIG. 4 is a diagram showing one example of a screen showing substance group information according to the one embodiment;

FIG. 7 is a diagram showing one example of a screen, according to a modified example, showing substance information or substance group information, about each substance group;

FIG. 8 is a diagram showing one example of a screen, according to a modified example, showing substance information and substance group information, about each substance group.

DETAILED DESCRIPTION

Figure 1:
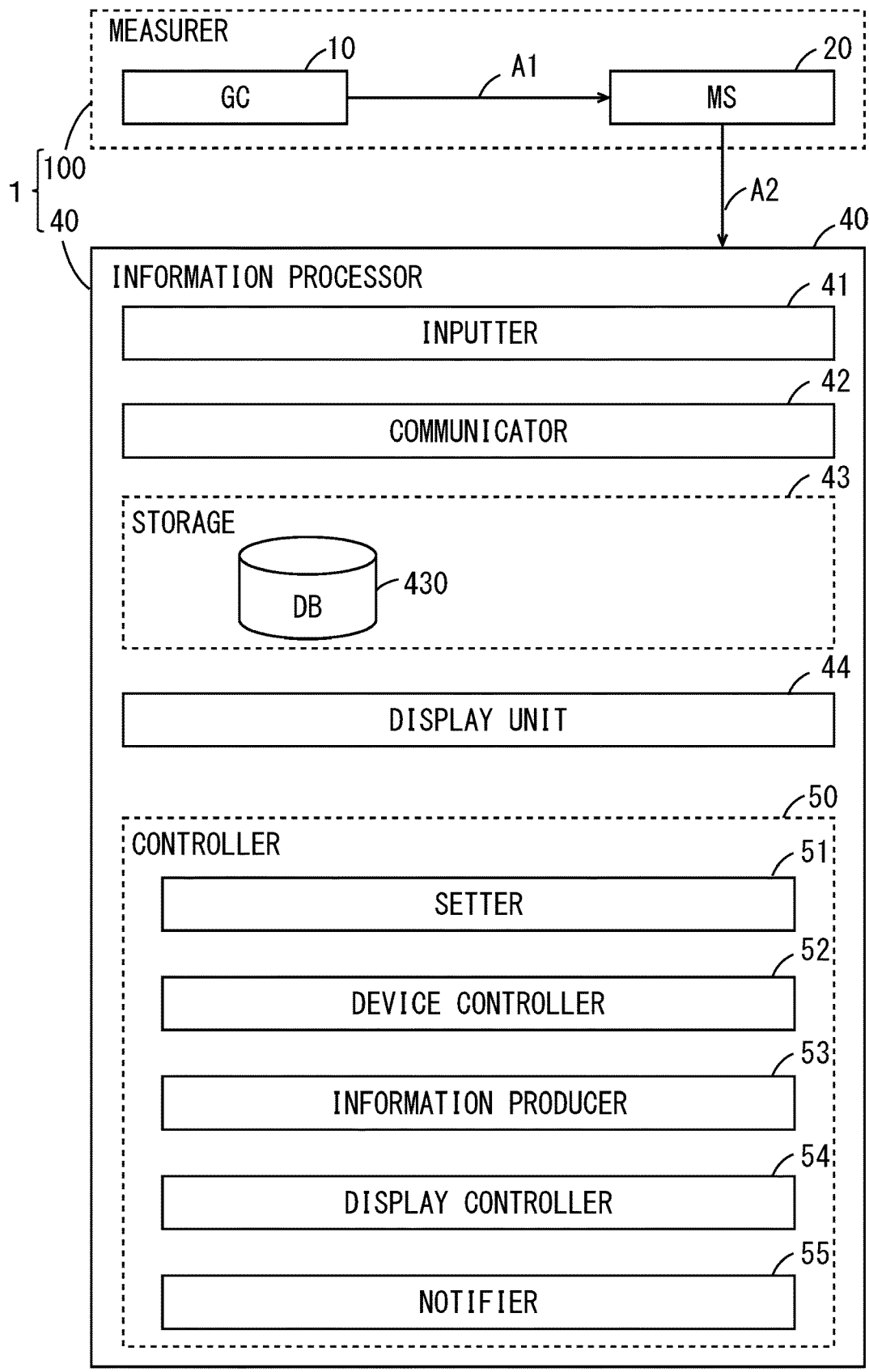
FIG. 1 is a conceptual diagram showing the configuration of an analysis device of one embodiment.

Embodiments of the present invention will be described below with reference to the drawings.

Embodiments

An analysis device of the present embodiment analyzes a substance group including a plurality of different substances in regard to a sample and displays information about each of the plurality of different substances and the substance group. Hereinafter, the information about each of the plurality of difference substances is referred to as substance information, and the information about the substance group is referred to as substance group information.

In regard to each substance, the substance information can include any information defined for each substance such as the name of the substance, its characteristics or a parameter used for an analysis of the substance. For example, the substance information can include a number or a symbol, which represents a substance, and the name of the substance, a parameter used for an analysis of the substance or a numerical value obtained by an analysis of the substance that are associated with the above-mentioned number or symbol.

In regard to each substance group, the substance group information can include any information defined for each substance group such as the name of the substance group, its characteristics or the number of substances included in the substance group. The substance group information can include the name of the substance group or the number of types of substances included in the substance group. Alternatively, in regard to substances included in the substance group, the substance group information can include the number or the names of types of substances detected in an analysis, or a summed value of amounts or concentrations of the substances detected in the analysis. The substance group information can include any combination of the above-mentioned items. The substance group information can include a number or a symbol, which represents a substance group and is associated with each above-mentioned item, for example.

A suitable example of a substance group to be analyzed includes PBDE, described above, and Polybromobiphenyl (PBB). In these cases, each molecule determined by the positions and the number of bromine atoms is a substance to be analyzed, and entire PBDE or entire PBB can be a substance group to be analyzed. Similarly to PBDE, an upper limit value for a concentration of PBB in each component that constitutes an electrical/electronic product is set by the EU RoHS directive. Similarly to PBDE and PBB, in a case where a summed value of amounts or concentrations of a plurality of substances included in an article is subject to regulation, the information relating to the regulation can be displayed by the analysis device 1 of the present embodiment in a comprehensible manner, thereby being useful. Examples of such regulation include PBDE and PBB regulated by the China RoHS directive and the Gulf Technical Regulation in addition to the above-mentioned RoHS directive, and phthalate esters regulated by the EU REACH (Registration, Evaluation, Authorisation and Restriction of Chemicals) regulation.

A substance group and substances included in the substance group can be in various other forms. A plurality of different substances may be grouped into substance groups based on characteristics of substances such as volatility, semi-volatility or non-volatility. In this case, a plurality of different substances having predetermined volatility can be defined as a substance group by a label such as a "volatile substance group." Substances may be grouped based on their use, field or the like and can be grouped into groups such as plasticizers, flame retardants, antioxidants or the like. To which substance group each substance belongs can be suitably set by an analyst or a user of an analysis device.

(Regarding Analysis Device)

FIG. 1 is a conceptual diagram showing the configuration of the analysis device according to the present embodiment. The analysis device 1 is a Gas Chromatograph-Mass Spectrometer (GC-MC). The analysis device 1 includes a measurer 100 and an information processor 40.

The measurer 100 includes a Gas Chromatograph (GC) 10 and a Mass Spectrometer (MS) 20.

The information processor 40 includes an inputter 41, a communicator 42, a storage 43, a display unit 44 and a controller 50. The storage 43 includes a substance DB 430. The controller 50 includes a setter 51, a device controller 52, an information producer 53, a display controller 54 and a notifier 55.

The measurer 100 performs each operation (hereinafter referred to as an analysis operation) in an analysis of a sample, and obtains and detects each component of the sample by separation. The sample is introduced into the GC 10.

As long as the analysis device 1 can analyze the sample and the sample may include a substance group to be analyzed, the sample is not limited in particular.

The GC 10 separates the sample into components using gas chromatography. The GC 10 vaporizes the introduced sample or makes the introduced sample be gaseous. A gas sample, or a vaporized or gaseous sample is referred to as a sample gas. The GC 10 separates the sample gas in a separation column. Each component of the separated sample is eluted from the separation column at different retention times. Each component of the eluted sample is introduced into the MS 20 (the arrow A1).

The MS20 performs mass spectrometry of the introduced sample. The MS 20 ionizes the introduced sample by an ionizer (not shown). The ionized sample is referred to as sample-derived ions. The MS 20 performs mass separation on the sample-derived ions by a mass spectrometry device (not shown) and detects the sample-derived ions by an ion detector (not shown). The MS 20 may perform modification, dissociation or the like on the sample-derived ions and may perform mass separation on ions obtained by modification or dissociation to detect the ions. The ions obtained by modification or dissociation are also included in the sample-derived ions.

The MS 20 converts a detection signal obtained by detection of the sample-derived ions into a digitalized signal by an Analog/Digital (A/D) converter (not shown) and outputs the digitalized detection signal to the information processor 40 (the arrow A2). Hereinafter, data including an intensity of a detection signal of sample-derived ions obtained by an analysis operation performed by the measurer 100 as detection data.

As long as being able to detect sample-derived ions with desired accuracy by mass spectrometry, the type of a mass spectrometer that constitutes the MS 20 is not limited in particular. Any one or more types of mass spectrometry devices can be used.

The information processor 40 includes an information processing apparatus such as an electronic calculator and executes processes such as communication, storage or calculation in regard to various data in addition to serving as an interface with respect to a user of the analysis device 1 (hereinafter simply referred to as a "user.") The information processor 40 functions as a processing apparatus for processing information relating to an analysis.

The inputter 41 includes an input device such as a mouse, a keyboard, various buttons or a touch panel. The inputter 41 receives information required for a process executed by the controller 50 from the user. The communicator 42 includes a communication device that can communicate via wireless connection or wired communication such as the Internet, and suitably transmits and receives data and so on relating to a process executed by the controller 50.

The storage 43 includes a storage medium and stores a program and data for execution of a process by the controller 50. A program for execution of a process by the below-mentioned display controller 54 is included in this program. Part of data used by the analysis device 1 may be saved in a remote server or the like, and at least part of a calculation process executed by the above-mentioned program may be executed in the remote server or the like.

The substance DB 430 of the storage 43 is a DB including substance data. In the substance data of the present embodiment, substance information required for an analysis is stored. The substance data may be stored in the substance DB 430 in advance or may be acquired by user's input or communication with an external device.

FIG. 2 is a diagram showing a chart A that schematically shows the contents of the substance DB 430. In the chart A, the contents shown in the same row are associated with one another in the substance DB 430. The chart A shows an item C11 for the name of a substance group, an item C12 for the name of a substance, an item C13 for a first retention time, an item C14 for first target ions, an item C15 for first qualifier ions and an item C16 for a first ion ratio. While the item C11 for the name of a substance group is arranged at the leftmost position in the chart A, each value is set for each substance shown in the item C12 for the name of a substance.

As shown in the chart A, the below-mentioned display controller 54 can cause the display unit 44 to display the items in association with one another. The chart A is one example of a display screen of the display unit 44. In this case, design such as presence or absence of a vertical line or a horizontal line is not limited in particular.

The item C11 for the name of a substance group shows the name of a substance group to which a substance, in the item C12 for the name of a substance, belongs. The item C12 for the name of a substance shows the name of a substance. To which substance group each substance belongs is set by the item C11 for the name of a substance group and the item C12 for the name of a substance.

The item C13 for a first retention time shows a retention time that is set for detection of a substance in mass spectrometry. The item C14 for first target ions shows m/z that is set for detection of target ions of a substance by mass spectrometry. Among sample-derived ions that are derived from a substance, target ions are the ions that are to be suitably detected from a quantitativity point of view, etc. The item C16 for first qualifier ions shows m/z that is set for detection of qualifier ions of a substance by mass spectrometry. Among sample-derived ions that are derived from the substance, qualifier ions have specificity in regard to a substance although not being used for a quantitative analysis of the substance. Reliability of data about target ions is enhanced by confirmation of detection of qualifier ions. The m/z of target ions and the m/z of qualifier ions are set based on data obtained by a past analysis, a theoretical value on the basis of these amino acid sequences or the like. In the following description, the term a "mass-to-charge ratio" is interpreted in a broad sense and is a parameter indicating a ratio with respect to a charge of mass, and m/z is used as one example of the parameter. However, a mass-to-charge ratio of different unit or the like can be used instead of m/z.

The item C16 for a first ion ratio shows a qualifier ion ratio. A qualifier ion ratio is a ratio between a detection intensity of target ions and a detection intensity of qualifier ions. A detection intensity is a value representing the intensity of a detection signal of ions. In a case where a qualifier ion ratio is close to a set value in addition to confirmation of detection of qualifier ions, reliability of data about target ions is further enhanced. A set value of a qualifier ion ratio is set based on a value obtained by mass spectrometry of the substance in the past or the like.

Substance information used for an analysis is not limited to the information shown in the chart A, and any numerical value or matter relating to an analysis can be used.

Returning to FIG. 1, the display unit 44 is configured to include a display device such as a liquid crystal monitor. The display unit 44 displays the information and so on produced by the information producer 53 in the display device due to the control of the display controller 54.

The controller 50 includes a processor such as a CPU (Central Processing Unit) and a storage medium such as a memory. The processor behaves as a main constituent of the analysis device 1 by reading a program stored in the storage 43 or the like into a memory for execution, controlling the measurer 100, processing detection data, etc.

As long as being able to execute a process to be executed by the controller 50 according to the present embodiment, the physical configuration of the controller 50 is not limited in particular.

The setter 51 of the controller 50 sets grouping of a plurality of different substances into substance groups based on user's input. For example, the user can create or change any substance group via the setter 51 by inputting or selecting a plurality of different substances on a screen and inputting a name, a reference number or the like of a corresponding substance group. The user can set a substance group via the setter 51 in this manner, so that it is possible to examine data and display a result of examination more flexibly.

The device controller 52 of the controller 50 controls an analysis operation executed by each part of the measurer 100. The device controller 52 sets a substance and a substance group to be analyzed based on user's input, or the like. The device controller 52 searches in the substance DB 430 and acquires parameters (a set retention time, m/z of target ions, m/z of qualifier ions, a qualifier ion ratio and so on in the chart A) required for separation and detection of substances to be analyzed. The device controller 52 controls each part of the measurer 100 using the acquired parameters and executes an analysis operation. For example, the device controller 52 acquires a set retention time (Ta) and m/z (Qa) of qualifier ions corresponding to a substance A from the substance DB 430. The device controller 52 controls the measurer 100 such that mass separation is performed on ions having the m/z (Qa) at the retention time Ta, and detects target ions corresponding to the substance A.

The information producer 53 of the controller 50 produces substance information and substance group information from the detection data obtained in an analysis of a sample. The information producer 53 calculates a detection intensity of sample-derived ions corresponding to each substance to be analyzed from the substance DB 430 and the detection data. For example, the information producer 53 produces data corresponding to a chromatogram in regard to m/z of a predetermined value or m/z in a predetermined range, or a mass spectrum at each retention time. The information producer 53 can set a maximum intensity or an area of a peak of qualifier ions and target ions in the chromatogram and mass spectrum as detection intensities of a substance corresponding to these data. Here, a chromatogram is a graph in which the abscissa indicates a retention time and the ordinate indicates an intensity of a substance detected at each retention time, and a mass spectrum is a graph in which the abscissa indicates m/z and the ordinate indicates an intensity of ions having each detected m/z.

The information producer 53 can calculate a qualifier ion ratio by calculating a ratio between a detection intensity of target ions and a detection intensity of qualifier ions. In a case where data for calibration such as a calibration carve is acquired, and a concentration of each substance in a sample can be calculated, the information producer 53 can convert a calculated detection intensity of each substance into a concentration. In a case where a detection intensity or a concentration of target ions exceeds a predetermined value based on noise or the like, the information producer 53 determines that a substance corresponding to the target ions are detected. The information producer 53 causes the storage 43 or the like to store each value obtained by the above-mentioned calculation for each substance. Further, the information producer 53 causes the storage 43 or the like to store whether each substance to be analyzed is detected in any data format such as binary in regard to each substance. The information representing whether each substance has been detected is referred to as detection information.

The information producer 53 produces substance group information based on data in the substance DB 430, a value obtained by the above-mentioned calculation performed by the information producer 53, etc. The information producer 53 acquires a plurality of different substances included in a substance group to be analyzed from the substance DB 430 and calculates the number of types of detected substances among the plurality of different substances. The information producer 53 calculates the sum of detection intensities or the sum of concentrations of the detected substances among the plurality of difference substances. The information producer 53 may calculate the number of types of the plurality of substances included in the substance group to be analyzed. The information producer 53 associates the above-mentioned calculated values with each substance group and causes the storage 43 or the like to store the above-mentioned calculated values as substance group information.

As described above, the information producer 53 executes a process of acquiring a plurality of different substances included in a substance group to be analyzed (referred to as a first process) and a process of calculating the number of types of detected substances among the plurality of different substances (referred to as a second process), for example, in order to produce substance group information. Further, the information producer 53 executes a process of calculating the sum of detection intensities or the sum of concentrations of the detected substances (hereinafter referred to as a third process) and a process of calculating the number of types of the plurality of substances included in the substance group to be analyzed (hereinafter referred to as a fourth process), for example. The above-mentioned first process to fourth process to be executed by the information producer 53 are examples of a statistical process of the present invention.

The information producer 53 can calculate any value not limited to the above-mentioned values but relating to an analysis as substance information or substance group information.

The display controller 54 of the controller 50 causes the display unit 44 to display substance information and substance group information. The display controller 54 in the present embodiment causes the display unit 44 to switchably display substance information and substance group information.

FIG. 3 is a conceptual diagram of screen elements representing substance information in the display screen of the display unit 44. The display screen or the screen elements shown in the following diagram is merely one example. As long as substance information about a substance is displayed for each substance, and substance group information about a substance group is displayed for each substance group, design such as presence or absence of a line or a horizontal line is not limited in particular.

A chart TS is shown in a first screen element SE1 of FIG. 3. In the chart TS, one row corresponds to one type of substance, and information relating to an analysis is shown in regard to each substance. In the chart TS, the item C11 for the name of a substance group, the item C12 for the name of a substance, an item C17 for detection, an item C130 for a second retention time, an item C18 for a concentration, an item C140 for second target ions, an item C150 for second qualifier ions and an item C160 for a second ion ratio are shown. While the item C11 for the name of a substance group is arranged at the leftmost position in the chart TS1, each value is displayed in regard to each substance shown in the item C12 for the name of a substance. In regard to the items that have already been explained such as the C11 for the name of a substance group, a description will not be repeated since their contents are the same. The same applies to each of the following charts.

The item C17 for detection shows detection information. In the item C17 for detection, a check mark is displayed in a case where each substance is detected in an analysis of a sample, and a hyphen is displayed in a case where each substance is not detected. As long as it is possible to distinguish between detection and non-detection in the item C17 for detection, the display pattern is not limited in particular.

The item C130 for a second retention time shows a retention time at which each substance is actually measured in an analysis of a sample. The item C18 for a concentration shows a concentration of each substance obtained in an analysis of a sample. The item C140 for second target ions shows a detection intensity (a peak area value in the chart TS) of target ions of each substance. The item C140 for second target ions shows a detection intensity (a peak area value in the chart TS) of qualifier ions of each substance. The item C160 for a second ion ratio shows a qualifier ion ratio of each substance.

FIG. 4 is a conceptual diagram of screen elements representing substance group information in the display screen of the display unit 44. A chart TG is shown in a second screen element SE2 of FIG. 4. In the chart TG, one row corresponds to one type of substance, and information relating to an analysis is shown in regard to each substance group. In the chart TG, an item C21 for the name of a substance group, an item C22 for the number of substances, an item C23 for the number of detected substances and an item C24 for a summed value are shown.

The item C21 for the name of a substance group shows the name of a substance group. In the chart TG, substance group information is shown in regard to each substance group of the item C21 for the name of a substance group. The item C22 for the number of substances shows the number of types of substances included in each substance group. The item C23 for the number of detected substances shows the number of types of detected substances among substances included in each substance group. The item C24 for a summed value shows a summed value of concentrations of substances included in each substance group. The item C24 for a summed value may show a summed value of not concentrations but detection intensities. In the example of FIG. 3, in regard to a substance group X, the concentration of a detected substance A is Ca, the concentration of a detected substance B is Cb, the concentration of a detected substance C is Cc and the concentration of a detected substance D is Cd. Therefore, the summed value of concentrations of the substance group X is a numerical value obtained by the formula Ca+Cb+Cc+Cd. While a substance group Y includes E, F, G and H from the example of FIG. 3, substances E and H are not detected. Therefore, the summed value of concentrations of the substance group Y is the sum of the concentration Cf of the detected substance F and the concentration Cg of the detected substance G.

The display controller 54 can display any value not limited to the above-mentioned value but relating to an analysis as substance information or substance group information.

The display controller 54 in the present embodiment switches the display between substance information and substance group information in regard to all of substance groups in one go.

Figure 5:
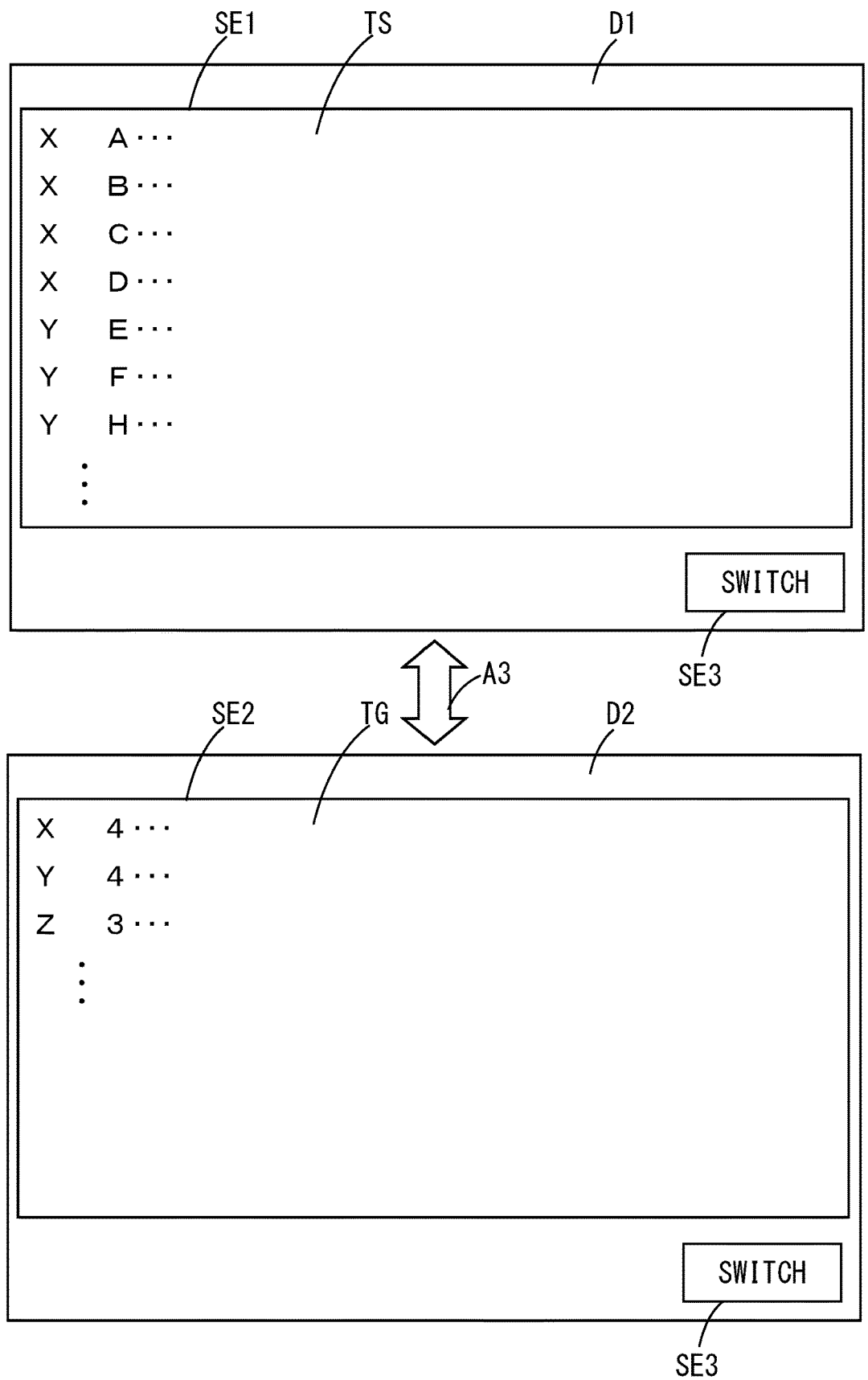
FIG. 5 is a conceptual diagram for explaining about switchably displaying substance information and substance group information.

FIG. 5 is a conceptual diagram showing the control of switch of the display screen by the display controller 54. Display screens D1 and D2 are screens showing a result obtained by an analysis and displayed by the display unit 44 due to the control of the display controller 54.

In the display screen D1, the first screen element SE1 and a third screen element SE3 are displayed. The first screen element SE1 is a screen element displaying characters, images and so on, and the chart TS (FIG. 3) showing substance information is displayed in the first screen element SE1. The third screen element SE3 is a button. In the display screen D2, the second screen element SE2 and the third screen element SE3 are displayed. The second screen element SE2 is a screen element displaying characters, images and so on, and the chart TG (FIG. 4) showing substance information is displayed in the second screen element SE2.

In a case where the display screen D1 is displayed, when the user clicks on the button of the third screen element SE3, the display controller 54 switches the display of the display screen D1 showing the substance information to the display of the display screen D2 showing the substance group information. In a case where the display screen D2 is displayed, when the user clicks on the button of the third screen element SE3, the display controller 54 switches the display of the display screen D2 showing substance group information to the display of the display screen D1 showing substance information. In FIG. 5, the switch between the display screens D1, D2 by the display controller 54 is schematically shown by the arrow A3.

In regard to all of substances or substance groups, the screen displaying substance information in regard to each substance and the screen displaying substance group information in regard to each substance group are switched by the control of the display controller 54. Thus, the user can view the information in regard to each substance and the information in regard to each substance group by suitably switching the screens as necessary. Therefore, the analysis device 1 can provide information about a substance group and substances included in the substance group in regard to an analysis of sample in a comprehensible manner. Further, the analysis device 1 can switch the display in regard to a plurality of substances or the large number of substances altogether, that is, in one go, so that the user can efficiently view the information about an analysis with a simple operation.

Although the third screen element SE3 is a button, as long as the third screen element SE3 can detect user's action in regard to a switching instruction, its form is not limited in particular. For example, the display controller 54 is configured to perform the above-mentioned switch when the user clicks on the first screen element SE1 or the second screen element SE2. Alternatively, the display controller 54 may be configured to perform the above-mentioned switch in a case where an option for performing the above-mentioned switch is selected from among the options displayed by the user's right-click. Further, although being able to be switched bidirectionally, the screen showing substance information and the screen showing substance group information may be configured to be switched unidirectionally.

The notifier 55 of the controller 50 provides a notification in a case where a substance group to be analyzed is subject to regulation and a result not complying with the regulation is obtained by an analysis of a sample. The notifier 55 makes reference to a threshold value based on the regulation that is stored in advance in the storage 43 or the like. In a case where the upper limit in regard to an amount of a substance group included in an article is subject to regulation, when a summed value of detection intensities or concentrations of substances included in a substance group exceeds a threshold value, the notifier 55 provides a notification that the article violates or may violate the regulation. As long as whether an article complies with the regulation is determined based on a condition on the basis of a threshold value, the manner of determination is not limited in particular. The manner of notification provided by the notifier 55 is not limited in particular. Characters or an image may be displayed in the display unit 44 by a pop-up message or the like, or warning may be provided by voice. In a case where a summed value of detection amounts or concentrations of a plurality of different substances corresponding to a substance group satisfies a condition based on a threshold value, the notifier 55 provides a notification. Therefore, in regard to the substance group to be analyzed, the user can be notified of information about whether an article according to a sample complies with regulation in a comprehensible manner.

The notifier 55 may be configured to provide a notification in a case where the number of a plurality of different detected substances corresponding to a substance group satisfies a condition based on a threshold value.

(Regarding Analysis Method)

Figure 6:
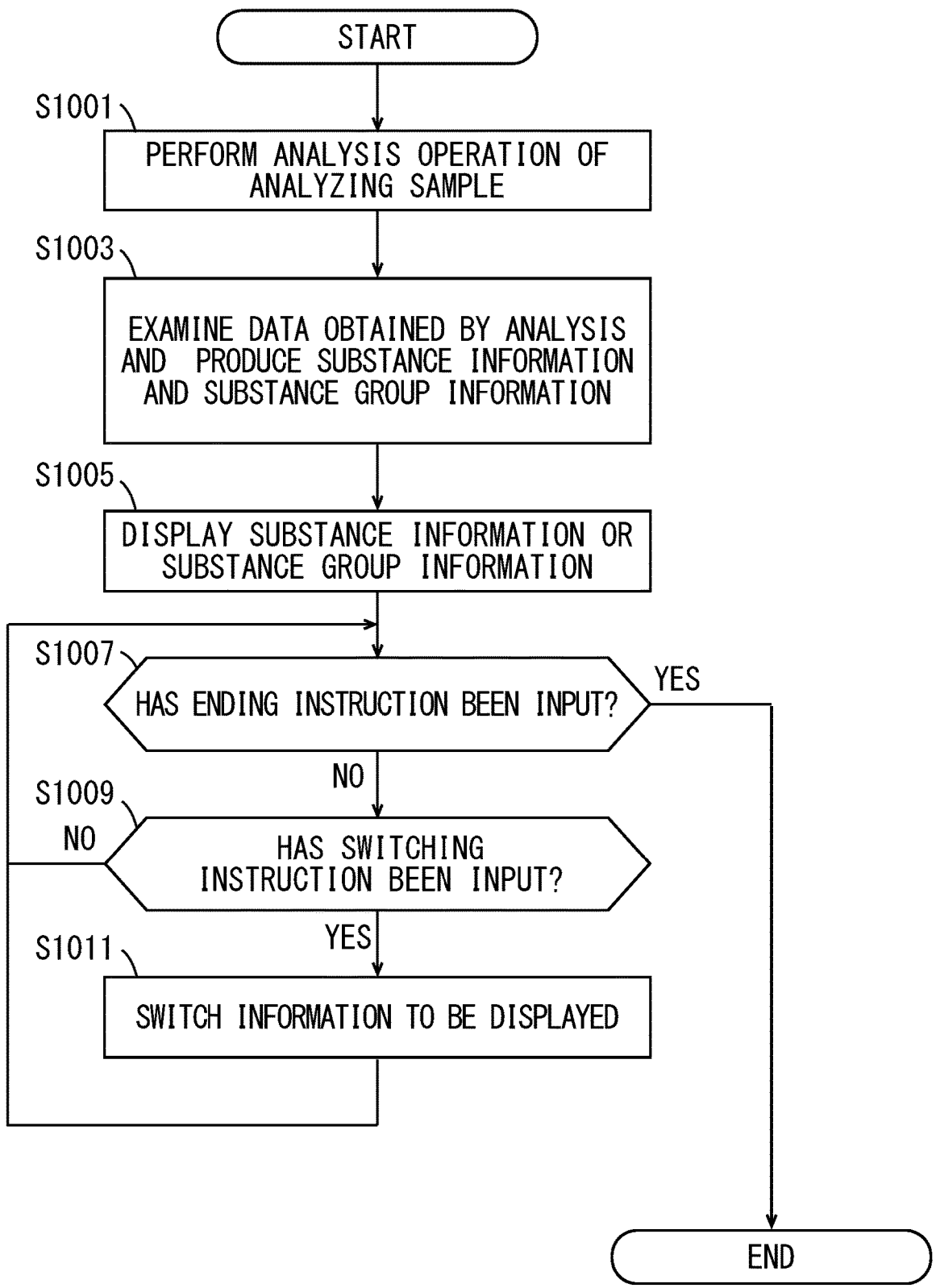
FIG. 6 is a flowchart showing a flow of an analysis method according to the one embodiment.

FIG. 6 is a flowchart showing a flow of an analysis method including a display method according to the present embodiment of displaying information relating to an analysis. In the step S1001, the device controller 52 controls the measurer 100 and performs an operation of analyzing a sample. When the step S1001 ends, the step S1003 is started.

In the step S1003, the information producer 53 examines data (detection data or the like) obtained by an analysis of a sample and produces substance information and substance group information. When the step S1003 ends, the step S1005 is started. In the step S1005, the display controller 54 controls the display unit 44 and displays the substance information or the substance group information. When the step S1005 ends, the step S1007 is started.

In the step S1007, the display controller 54 determines whether an ending instruction is provided by the user. In a case where the ending instruction is input, affirmative determination is made in the step S1007, and the display controller 54 ends a process. In a case where the ending instruction is not input, negative determination is made in the step S1007, and the step S1009 is started.

In the step S1009, the display controller 54 determines whether a switching instruction is input by the user. In a case where the switching instruction is input, affirmative determination is made in the step S1009, and the step S1011 is started. In a case where the switching instruction is not input, negative determination is made in the step S1009, and the step S1007 is started. In the step S1011, the display controller 54 switches the information to be displayed between the substance information and the substance group information. When the step S1011 ends, the step S1007 is started.

With the above-mentioned embodiment, the following effects are obtained.

(1) The analysis device 1 of the present embodiment includes the display controller 54 that causes display unit 44 to display substance information, which is the information about each substance in regard to an analysis of a sample, and substance group information, which is the information about each substance group including a plurality of different substances in regard to the analysis, and the display controller 54 switchably displays the substance information and the substance group information. Thus, the analysis device 1 can provide information about a substance group and substances included in the substance group in regard to an analysis of a sample in a comprehensible manner.

(2) In the analysis device 1 of the present embodiment, the display controller 54 can switch the display between substance information and substance group information altogether, that is, in one go in regard to all of substance groups. Thus, the user can efficiently view the information about an analysis with a simple operation.

(3) In the analysis device 1 of the present embodiment, a plurality of different substances included in a substance group can be substances a summed value, of amounts or concentrations of the plurality of different substances included in an article, of which is subject to regulation. Thus, the analysis device 1 can provide information about whether the article complies with the regulation in a comprehensible manner.

Following modifications is in the scope of the present invention and can be combined with the above-mentioned embodiment. In the below-mentioned modified example, parts having structure and functions similar to those of the above-mentioned embodiment are denoted with the same reference numerals, and a description will suitably be not repeated.

MODIFIED EXAMPLE 1

In the above-mentioned embodiment, a sample is analyzed by Gas Chromatography/Mass spectrometry (GC/

MS), by way of example. However, as long as information about a substance group can be produced from an obtained result of analysis in regard to each substance, the type of analysis is not limited in particular. An analysis of a sample can include mass spectrometry, chromatography, chromatography/mass spectrometry, pyrolysis gas chromatography and pyrolysis GC/MS. From a similar point of view, an analysis device that analyzes a sample can include a mass spectrometer, a chromatograph, a chromatograph-mass spectrometer, a pyrolysis GC and a pyrolysis GC-MS.

MODIFIED EXAMPLE 2

In the above-mentioned embodiment, the display controller 54 is configured to switch the display between the substance information and the substance group information in regard to all of substance groups altogether, that is, in one go. However, the display controller 54 may be configured to perform the above-mentioned switch in regard to one or a plurality of substance groups. One or a plurality of substance groups subject to a switch is preferably determined by selection made by the user.

FIG. 7 is a conceptual diagram showing one example of a display screen in the present modified example. A fourth screen element SE4 is a screen element displaying characters, images and so on, and a chart TG1 showing substance group information about a substance group X and a chart TS1 showing substance information about substance groups Y, Z are displayed in the fourth screen element SE4. The fourth screen element SE4 is a screen element that shows a result of analysis and is displayed by the display unit 44 due to the control of the display controller 54.

The display controller 54 switches the display between the substance information and the substance group information in regard to a selected substance group.

The display controller 54 displays the first screen element SE1 showing the substance information shown in FIG. 3 in the display unit 44. When the user clicks on a region corresponding to the substance group X on a screen, the display controller 54 displays the chart TG1 showing the substance group information about the substance group X instead of the substance information about the substance group X, that is, displays the fourth screen element SE4. The chart TG1 is a section corresponding to the substance X in the chart TG showing the substance group information (see FIG. 4). When the user clicks on a region corresponding to the substance X in the chart TG1 with the fourth screen element SE4 displayed, the display controller 54 displays the substance information about the substance group X instead of the substance group information about the substance group X. That is, the first screen element SE1 is displayed again.

Also in regard to other substance groups to be analyzed such as the substance groups Y, Z, the display controller 54 similarly switches the display between the substance information and the substance group information by the user's click.

The display controller 54 may be configured to switch the display between the substance information and the substance group information at the same time in regard to a plurality of substance groups. In this case, the user may select a plurality of substance groups subject to a switch of display by using a check box, a toggle button or the like corresponding to each substance group. For example, it is possible to display the fourth screen element SE4 of FIG. 7 by switching the display between the substance groups Y, Z in the second screen element SE2 of FIG. 4, or vice versa.

Further, a method of selecting a substance group subject to a switch of display is not limited in particular. For example, options for substance groups may be displayed by the user's right-click, and the display controller 54 may be configured to switch the display in regard to a selected substance group.

In the analysis device 1 of the present modified example, the display controller 54 switches between the substance information and the substance group information in regard to one or a plurality of selected substance groups. Thus, it is possible to flexibly set contents to be displayed for each substance group and provide information in a manner that suits a user's request.

MODIFIED EXAMPLE 3

In the above-mentioned embodiment, the display controller 54 is configured to display either substance information or substance group information in the display screen. However, the display controller 54 may be configured to switch between a display and a non-display of substance group information in addition to a display of substance information.

FIG. 8 is a conceptual diagram showing one example of a display screen in the present modified example. A fifth screen element SE5 is a screen element that displays characters, images and so on. In the fifth screen element SE5, charts TSX, TGX that respectively show substance information and substance group information about a substance group X and charts TSY, TGY that respectively show substance information and substance group information about a substance group Y are displayed. The fifth screen element SE5 is a screen element that shows a result of analysis and is displayed by the display unit 44 due to the control of the display controller 54.

The display controller 54 causes the display unit 44 to display the display screen D1 shown in the upper field of FIG. 5. In the display screen D1, the substance information of each substance is displayed in the first screen element SE1, and the substance group information is not displayed. When the user clicks on the button of the third screen element SE3, the display controller 54 displays the fifth screen element SE5 showing the substance group information about each substance group together with the substance information instead of the first screen element SE1. In other words, the display controller 54 adds the charts TGX, TGY respectively showing the substance group information about the substance groups X, Y to the first screen element SE1. Alternatively, the display controller 54 adds a row or a column that shows the substance group information and corresponds to each substance group to the chart representing the substance information. In this example, a display and a non-display of the substance group information about each substance group can be switched with a simple operation.

In a case where substance information and substance group information are displayed together in the fifth screen element SE5, the substance information and the substance group information are preferably displayed to be adjacent to each other in regard to each substance as shown in FIG. 8. However, the invention is not limited to this.

As described above in the modified example 2, the display controller 54 may be configured to switch between a display and a non-display of substance group information in regard to one or a plurality of substance groups. A substance group subject to this switch is preferably set by selection made by the user. In this case, information can be displayed flexibly in accordance with a user's request. Further, as described above, a method of selecting a substance group subject to a switch of display is not limited in particular.

In the analysis device 1 of the present modified example, the display controller 54 displays substance information such that a display and a non-display of substance group information can be switched. In other words, the display controller 54 is configured to switch between a display and a non-display of substance group information when displaying substance information. Thus, the analysis device 1 can provide information about a substance group and substances included in the substance group in regard to an analysis of a sample in a comprehensible manner.

MODIFIED EXAMPLE 4

In the above-mentioned embodiment, part or all of a plurality of different substances may be included in a plurality of different substance groups. Thus, the user can flexibly set a substance group and perform more in-depth examination of data. In a case where an amount or concentration of a substance group included in an article is regulated, different substance groups can be set in accordance with a plurality of different regulations in regard to the same substance, and whether the substance complies with each regulation can be examined appropriately.

MODIFIED EXAMPLE 5

A program for implementing an information processing function of the analysis device 1 may be recorded in a computer-readable recording medium. A computer system may read the program, which is recorded in the recording medium, in regard to a process to be executed by the controller 50 including the above-mentioned process of the display controller 54 and the control of its related process and execute the program. A "computer system" here includes hardware such as an OS (Operating System) or peripheral appliances. Further, a "computer-readable recording medium" refers to a movable recording medium such as a flexible disc, an optical magnetic disc, an optical disc or a memory card and a storage device such as a hard disc or a Solid State Drive (SSD) built into the computer system. Further, a "computer-readable recording medium" may include an object that retains a program movably for a short period of time such as a communication wire that is used when a program is transmitted through a network such as the Internet or a communication line such as a telephone line, or an object that retains a program for a certain period of time such as a volatile memory in a computer system that serves as a server or a client. Further, the above-mentioned program may be to implement part of the above-mentioned functions and may further be to implement the above-mentioned functions by being combined with a program that has already been recorded in the computer system.

Figure 9:
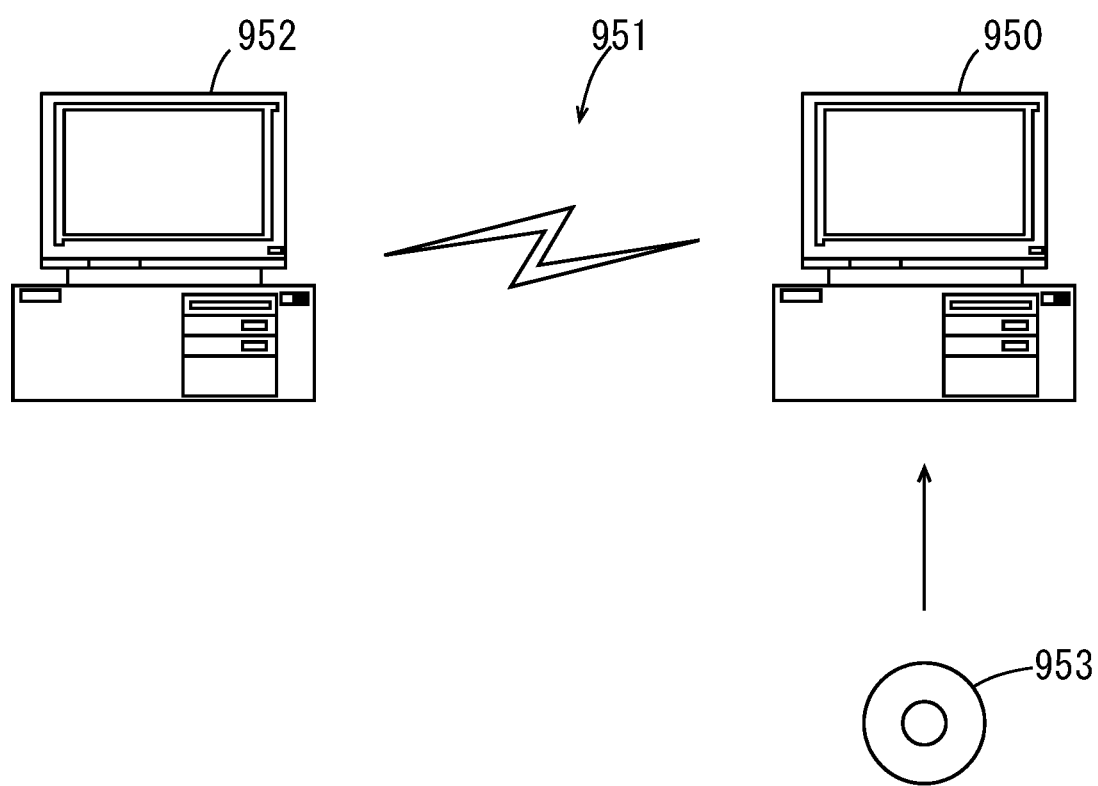
FIG. 9 is a conceptual diagram for explaining provision of a program.

Further, in a case where being applied to a personal computer (hereinafter referred to as a PC), the program relating to the above-mentioned control can be provided via a recording medium such as a CD-ROM or a DVD-ROM, or a data signal such as the Internet. FIG. 9 is a diagram showing the appearance. A PC 950 receives a program via a CD-ROM 953. Further, the PC 950 has a function to be connected to a communication line 951. The computer 952 is a server computer that provides the above-mentioned program and stores the program in a recording medium such as a hard disc. The communication line 951 is a communication line such as the Internet or a personal computer communication, or a dedicated communication line. The computer 952 reads a program with the use of the hard disc and transmits the program to the PC 950 through the communication line 951. That is, the program is transported by a carrier wave as a data signal and transmitted through the communication line 951. In this manner, the program can be provided as a computer-readable computer program product in various forms such as a recording medium or a carrier wave.

(Aspects)

It is understood by those skilled in the art that the plurality of above-mentioned illustrative embodiments or modified examples are specific examples of the below-mentioned aspects.

(Item 1) A processing apparatus according to one aspect (the information processor 40) for processing information relating an analysis includes a display controller that causes a display device to display first information (the substance information), which is information about each substance in regard to the analysis of a sample, and second information (the substance group information) which is information about each substance group including a plurality of the different substances in regard to the analysis, wherein the display controller displays the first information and the second information to be switchable to each other or displays the first information such that a display and a non-display of the second information are switchable. Thus, the processing apparatus can provide information about a substance group and substances included in the substance group in regard to an analysis of a sample in a comprehensible manner.

(Item 2) In the processing apparatus according another aspect for processing information relating to an analysis, the processing apparatus of the aspect of the item 1 processes information relating to an analysis, wherein the second information can include at least one of a number of the plurality of the different substances, a number of the plurality of the different substances detected in the analysis, a name representing a substance detected in the analysis and a summed value of detection amounts or concentrations of the plurality of the different substances in the analysis, in the substance group. Thus, the processing apparatus can provide these important information in a comprehensible manner when a result of analysis of a substance group is considered.

(Item 3) The processing apparatus according to the other aspect for processing information relating to an analysis, the processing apparatus of the aspect of the item 1 or 2 processes information relating to an analysis, wherein the display controller can perform at least one of a switch between the first information and the second information and a switch between a display and a non-display of the second information, in regard to one or a plurality of selected substance groups. Thus, the processing apparatus can flexibly display information in accordance with user's needs.

(Item 4) In the processing apparatus according to the other aspect for processing information relating to an analysis, the processing apparatus of the aspect of the item 1 or 2 processes information relating to an analysis, wherein the display controller can perform at least one of a switch between the first information and the second information and a switch between a display and a non-display of the second information, in one go in regard to all of substance groups. Thus, the user can switch the display with a simple operation and view information efficiently.

(Item 5) In the processing apparatus according to the other aspect for processing information relating to an analysis, the processing apparatus of the aspect of any one of the items 1 to 4 processes information relating to an analysis, wherein the display controller can switchably display a row or a column showing the second information in addition to a chart showing the first information. Thus, the user can flexibly adjust presence or absence of display of information about a substance group while viewing information about substances.

(Item 6) In the processing apparatus according to the other aspect for processing information relating to an analysis, the processing apparatus of the aspect of any one of the items 1 to 5 processes information relating to an analysis, wherein part or all of the plurality of the different substances can be included in a plurality of the substance groups. Thus, even in a case where a substance belongs to a plurality of substance groups, the processing apparatus can provide information about a substance group and substances included in the substance group in regard to an analysis of a sample in a comprehensible manner.

(Item 7) In the processing apparatus according to the other aspect for processing information relating to an analysis, the processing apparatus of the aspect of any one of the items 1 to 6 for processing information relating to an analysis can include a notifier that provides a notification in a case where a summed value of detection amounts or concentrations of the plurality of the different substances in the substance group or a number of the plurality of the different substances detected in the substance group, satisfies a condition based on a threshold value. Thus, the processing apparatus can notify the user of the relationship between an amount or a concentration of a substance group, and a threshold value in regard to the substance group to be analyzed in a comprehensible manner.

(Item 8) In the processing apparatus according to the other aspect for processing information relating to an analysis, the processing apparatus of the aspect of any one of the items 1 to 7 for processing information relating to an analysis can include a setter that sets grouping of a plurality of different substances into substance groups based on user's input. Thus, the user can flexibly set a substance group as necessary and perform more in-depth examination of data.

(Item 9) In the processing apparatus according to the other aspect for processing information relating to an analysis, the processing apparatus of the aspect of any one of the items 1 to 8 processes information relating to an analysis, wherein the plurality of the different substances can be substances a summed value, of amounts or concentrations of the different substances included in an article, of which is subject to regulation. Thus, from a regulation's point of view, information about a substance group in a sample can be provided in a comprehensible manner.

(Item 10) In the processing apparatus according to the other aspect for processing information relating to an analysis, the processing apparatus of the aspect of any one of the items 1 to 9 processes information relating to an analysis, wherein the analysis includes at least one of mass spectrometry, chromatography, pyrolysis gas chromatography, chromatography/mass spectrometry, pyrolysis gas chromatography/mass spectrometry. Thus, even in a case where a sample includes various types of molecules, it is possible to dissociate these molecules and accurately detect substances included in a substance group to be analyzed.

(Item 11) An analysis device according to one aspect includes the processing apparatus of the aspect of any one of the items 1 to 10 for processing information relating to an analysis. Thus, the analysis apparatus can analyze a sample and provide information about a substance group in the sample and substances included in the substance group in a comprehensible manner.

(Item 12) A display method according to one aspect of displaying information obtained by an analysis includes causing a display device to display first information (the substance information), which is information about each substance in regard to an analysis of a sample, and second information (the substance group information), which is information about each substance group including a plurality of the different substances in regard to the analysis, wherein in a display, the first information and the second information are displayed to be switchable to each other, or the first information is displayed such that a display and a non-display of the second information is switchable. Thus, information about a substance group and substances included in the substance group can be provided in a comprehensible manner.

(Item 13) A non-transitory computer readable medium according to one aspect stores a program for causing a computer to execute a display process (the steps S1005 to 1011 of the flowchart of FIG. 6) of causing a display device to display first information (the substance information), which is information about each substance in regard to an analysis of a sample, and second information (substance group information), which is information about each substance group including a plurality of the different substances in regard to the analysis, wherein the display process includes a process of causing the display device to display at least one of the first information and the second information such that the first information and the second information are displayed to be switchable to each other or the first information is displayed with the second information being switchable to be displayed or not to be displayed. Thus, the computer can provide information about a substance group and substances included in the substance group in regard to an analysis of a sample in a comprehensible manner.

The present invention is not limited to the contents of the above-mentioned embodiment. Other embodiments are possible without departing from the spirit and scope of the present invention.

While preferred embodiments of the present disclosure have been described above, it is to be understood that variations and modifications will be apparent to those skilled in the art without departing the scope and spirit of the present disclosure. The scope of the present disclosure, therefore, is to be determined solely by the following claims.

I claim:

1. A display method of displaying information relating to an analysis, of displaying information obtained from an analysis device for quantitatively analyzing a specific substance included in a sample, including:

displaying a set of substance groups and information associated with each substance group, wherein the associated information includes at least one name of a substance included in the substance group, at least one retention time of the substance group, a mass-to-charge ratio of target ions of the substance group, a mass-to-charge ratio of qualifier ions of the substance group, and a ratio between the detection intensity of the target ions and the qualifier ions;

receiving selection of at least one substance group of the set of substance groups, and at least one substance to be analyzed, wherein the specific substance is included in the at least one substance to be analyzed;

performing, for each selected substance group, mass separation on ions contained in the sample based on the mass-to-charge ratio of target ions of the substance group, the mass-to-charge ratio of qualifier ions of the substance group, and the ratio between the detection intensity of the target ions and the qualifier ions associated with the selected substance group;

acquiring analysis information including a plurality of information pieces of the specific substance using the analysis device based on results of the mass separation;

classifying the analysis information into pre-registered substance groups such that each pre-registered substance group includes a plurality of different substances, executing a statistical process of at least part of the first analysis information in regard to each pre-registered substance group, and creating second information in regard to each pre-registered substance group based on a result of the statistical process; and a screen display step of displaying at least one information out of the analysis information and the second information on a screen, wherein the screen display step includes receiving a display pattern selected by a user from among a pattern in which the analysis information and the second information are displayed at a same time on the screen, a pattern in which only the analysis information is displayed on the screen and a pattern in which only the second information is displayed on the screen, and changing a display pattern on the screen such that at least one information out of the analysis information and the second information is displayed in accordance with the received display pattern; and wherein the entireties of the analysis information and the second information are displayed by a character string on the screen.

2. The display method according to claim 1 of displaying information relating to an analysis, wherein the pre-registered substance groups includes at least one of Polybrominated diphenyl ether, Polybromobiphenyl and a phthalate ester.

3. The display method according to claim 1 of displaying information relating to an analysis, wherein the second information includes at least one of a number of the plurality of the different substances, a number of the plurality of the different substances detected in the analysis, and a summed value of detection amounts or concentrations of the plurality of the different substances in the analysis, in the substance group.

4. The display method according to claim 1 of displaying information relating to an analysis, wherein the screen display step includes performing at least one of a switch between the analysis information and the second information and a switch between a display and a non-display of the second information, in regard to one or a plurality of selected substance groups.

5. The display method according to claim 1 of displaying information relating to an analysis, wherein the screen display step includes performing at least one of a switch between the analysis information and the second information and a switch between a display and a non-display of the second information, in one go in regard to all of substance groups.

6. The display method according to claim 1 of displaying information relating to an analysis, wherein the screen display step includes switchably displaying a row or a column showing the second information in addition to a chart showing the analysis information.

7. The display method according to claim 1 of displaying information relating to an analysis, wherein a plurality of the pre-registered substance groups are registered in advance, one substance group out of the plurality of the pre-registered substance groups includes the plurality of difference substances, and part or all of the plurality of different substances are included in another substance group out of the plurality of the pre-registered substance groups.

8. The display method according to claim 1 of displaying information relating to an analysis, further including providing a notification in a case where a summed value of detection amounts or concentrations of the plurality of the different substances in a substance group of the pre-registered substance groups or a number of the plurality of the different substances detected in a substance group of the pre-registered substance groups, satisfies a condition based on a threshold value.

9. The display method according to claim 1 of displaying information relating to an analysis, further including setting groupings of a plurality of different substances into substance groups based on user's input, and the creating the second information includes classifying the analysis information into the pre-registered substance groups based on the setting of the groupings.

10. The display method according to claim 1 of displaying information relating to an analysis, wherein based on a summed value of amounts or concentrations of the different substances included in an article being subject to a regulation, information relating to the regulation is included in the second information.

11. The display method according to claim 1 of displaying information relating to an analysis, wherein the analysis includes at least one of mass spectrometry, chromatography, pyrolysis gas chromatography, chromatography/mass spectrometry, pyrolysis gas chromatography/mass spectrometry.

12. A processing apparatus of processing information relating to an analysis, of displaying information obtained from an analysis device for quantitatively analyzing a specific substance included in a sample, comprising at least one processor and at least one memory, the memory containing computer programs that, when executed by the at least one processor, cause the processor to operate as:

a display controller that displays at least a set of substance groups and information associated with each substance group, wherein the associated information includes at least one name of a substance included in the substance group, at least one retention time of the substance group, a mass-to-charge ratio of target ions of the substance group, a mass-to-charge ratio of qualifier ions of the substance group, and a ratio between the detection intensity of the target ions and the qualifier ions;

a selection receiver that receives selection of at least one substance group of the set of substance groups, and at least one substance to be analyzed, wherein the specific substance is included in the at least one substance to be analyzed;

a mass separation controller that performs, for each selected substance group, mass separation on ions contained in the sample based on the mass-to-charge ratio of target ions of the substance group, the mass-to-charge ratio of qualifier ions of the substance group, and the ratio between the detection intensity of the target ions and the qualifier ions associated with the selected substance group;

an analysis information acquirer that acquires analysis information including a plurality of information pieces of the specific substance based on results of the mass separation;
a second information producer that classifies the analysis information into pre-registered substance groups such that each pre-registered substance group includes a plurality of different substances, executes a statistical process of at least part of the analysis information in regard to each pre-registered substance group and creates second information in regard to each pre-registered substance group based on a result of the statistical process; and
the display controller that displays at least one information out of the analysis information and the second information on a screen, wherein
the display controller receives a display pattern selected by a user from among a pattern in which the analysis information and the second information are displayed at a same time on the screen, a pattern in which only the analysis information is displayed on the screen and a pattern in which only the second information is displayed on the screen, and changes a display pattern on the screen such that at least one information out of the analysis information and the second information is displayed in accordance with the received display pattern; and
wherein the entireties of the analysis information and the second information are displayed by a character string on the screen.

13. A non-transitory computer readable medium storing a program for causing a computer to execute a display process of displaying information obtained from an analysis device for quantitatively analyzing a specific substance included in a sample on a screen, the display process including
a display process for displaying a set of substance groups and information associated with each substance group, wherein the associated information includes at least one name of a substance included in the substance group, at least one retention time of the substance group, a mass-to-charge ratio of target ions of the substance group, a mass-to-charge ratio of qualifier ions of the substance group, and a ratio between the detection intensity of the target ions and the qualifier ions;
a selection process for receiving selection of at least one substance group of the set of substance groups, and at least one substance to be analyzed, wherein the specific substance is included in the at least one substance to be analyzed;
a mass separation process for performing, for each selected substance group, mass separation on ions contained in the sample based on the mass-to-charge ratio of target ions of the substance group, the mass-to-charge ratio of qualifier ions of the substance group, and the ratio between the detection intensity of the target ions and the qualifier ions associated with the selected substance group;
a process of acquiring analysis information including a plurality of information pieces of the specific substance based on results of the mass separation;
a process of classifying the analysis information into pre-registered substance groups such that each pre-registered substance group includes a plurality of different substances, executing a statistical process of at least part of the analysis information in regard to each pre-registered substance group and creating second information in regard to each pre-registered substance group based on a result of the statistical process; and
a screen display process of displaying at least one information out of the analysis information and the second information on a screen, wherein
the screen display process includes
a process of receiving a display pattern selected by a user from among a pattern in which the analysis information and the second information are displayed at a same time on the screen, a pattern in which only the analysis information is displayed on the screen and a pattern in which only the second information is displayed on the screen, and
a process of changing a display pattern on the screen such that at least one information out of the analysis information and the second information is displayed in accordance with the received display pattern; and
wherein the entireties of the analysis information and the second information are displayed by a character string on the screen.

* * * * *